(12) United States Patent
Culver

(10) Patent No.: US 8,025,068 B2
(45) Date of Patent: Sep. 27, 2011

(54) FLOSSING AND ORAL HYGIENE TOOL

(76) Inventor: Karen Culver, Windsor, CA (US)

( * ) Notice: Subject to any disclaimer, the term of this patent is extended or adjusted under 35 U.S.C. 154(b) by 368 days.

(21) Appl. No.: 12/239,984

(22) Filed: Sep. 29, 2008

(65) Prior Publication Data
US 2009/0090380 A1 Apr. 9, 2009

Related U.S. Application Data

(60) Provisional application No. 60/978,036, filed on Oct. 5, 2007.

(51) Int. Cl.
A45D 44/18 (2006.01)
A61C 15/00 (2006.01)
(52) U.S. Cl. .......................... 132/309; 132/323
(58) Field of Classification Search .............. 132/309, 132/286, 308, 310, 321, 323, 324, 329, 326, 132/327; 15/21.1, 167.1, 167.2, 104.16, 15/111; D28/65, 66, 68
See application file for complete search history.

(56) References Cited

U.S. PATENT DOCUMENTS

| | | | | |
|---|---|---|---|---|
| 736,650 | A * | 8/1903 | Storms, Jr. | 132/309 |
| 893,345 | A * | 7/1908 | Monson | 132/309 |
| 1,485,519 | A * | 3/1924 | Nelson | 132/309 |
| 1,544,404 | A * | 6/1925 | Hummel | 15/246 |
| 1,656,823 | A * | 1/1928 | Katz et al. | 132/309 |
| 2,517,806 | A * | 8/1950 | Streiler | 132/309 |
| 2,708,762 | A * | 5/1955 | Kling et al. | 15/110 |
| 2,754,833 | A * | 7/1956 | Vecchio | 132/323 |
| 3,850,182 | A * | 11/1974 | Clark, Jr. | 132/309 |
| 4,016,891 | A * | 4/1977 | Kupperman et al. | 132/309 |
| 4,880,382 | A * | 11/1989 | Moret et al. | 433/118 |
| 5,365,956 | A * | 11/1994 | Guadiana | 132/309 |
| 5,438,726 | A * | 8/1995 | Leite | 15/105 |
| 5,483,982 | A | 1/1996 | Bennet et al. | |
| 5,490,530 | A * | 2/1996 | Snowden | 132/311 |
| 5,924,429 | A | 7/1999 | Morando | |
| 6,039,050 | A * | 3/2000 | Goldenberg | 132/309 |
| 6,095,157 | A | 8/2000 | Brown | |
| 6,129,090 | A | 10/2000 | Pillar et al. | |
| 6,389,634 | B1 * | 5/2002 | Devlin et al. | 15/110 |
| 6,772,770 | B1 | 8/2004 | Williams | |
| 6,826,797 | B1 * | 12/2004 | Chenvainu et al. | 15/110 |
| 6,993,804 | B1 * | 2/2006 | Braun et al. | 15/110 |
| 7,055,531 | B2 * | 6/2006 | Rehkemper | 132/322 |
| 2002/0121283 | A1 | 9/2002 | Piccolo et al. | |
| 2003/0005544 | A1 | 1/2003 | Felix | |
| 2003/0188761 | A1 | 10/2003 | Garcia et al. | |
| 2004/0040571 | A1* | 3/2004 | Williams et al. | 132/309 |
| 2004/0040572 | A1* | 3/2004 | Chodorow | 132/323 |

(Continued)

FOREIGN PATENT DOCUMENTS

DE 19850325 A1 5/2000

Primary Examiner — Todd Manahan
Assistant Examiner — Vanitha Elgart
(74) Attorney, Agent, or Firm — Edward S. Sherman

(57) ABSTRACT

A detachable device for improved dental hygiene supports and tensions dental floss above and beyond the bristles of the tooth brush so that flossing can occur using the bristle end of the tooth brush and avoid having the bristles interfere with the flossing process. In preferred embodiments the device is mechanically coupled to a sonic toothbrush to transmit sonic energy to the floss for improved cleaning. In other embodiments the device includes a tongue cleaning implement.

20 Claims, 7 Drawing Sheets

U.S. PATENT DOCUMENTS

| | | | |
|---|---|---|---|
| 2004/0134512 A1* | 7/2004 | Ding et al. | 132/323 |
| 2004/0187887 A1* | 9/2004 | Beckman | 132/309 |
| 2004/0237995 A1 | 12/2004 | Mualem | |
| 2005/0211262 A1* | 9/2005 | Raab | 132/309 |
| 2005/0211263 A1 | 9/2005 | Kuo | |
| 2006/0260635 A1 | 11/2006 | Dabney | |
| 2007/0062554 A1 | 3/2007 | Dougan et al. | |
| 2007/0100360 A1 | 5/2007 | Lee | |
| 2007/0151575 A1* | 7/2007 | De Masi | 132/309 |
| 2009/0188519 A1* | 7/2009 | VanBuskirk et al. | 132/309 |
| 2009/0314307 A1* | 12/2009 | Hohlbein et al. | 132/309 |
| 2010/0269280 A1* | 10/2010 | Thomas | 15/167.1 |

\* cited by examiner

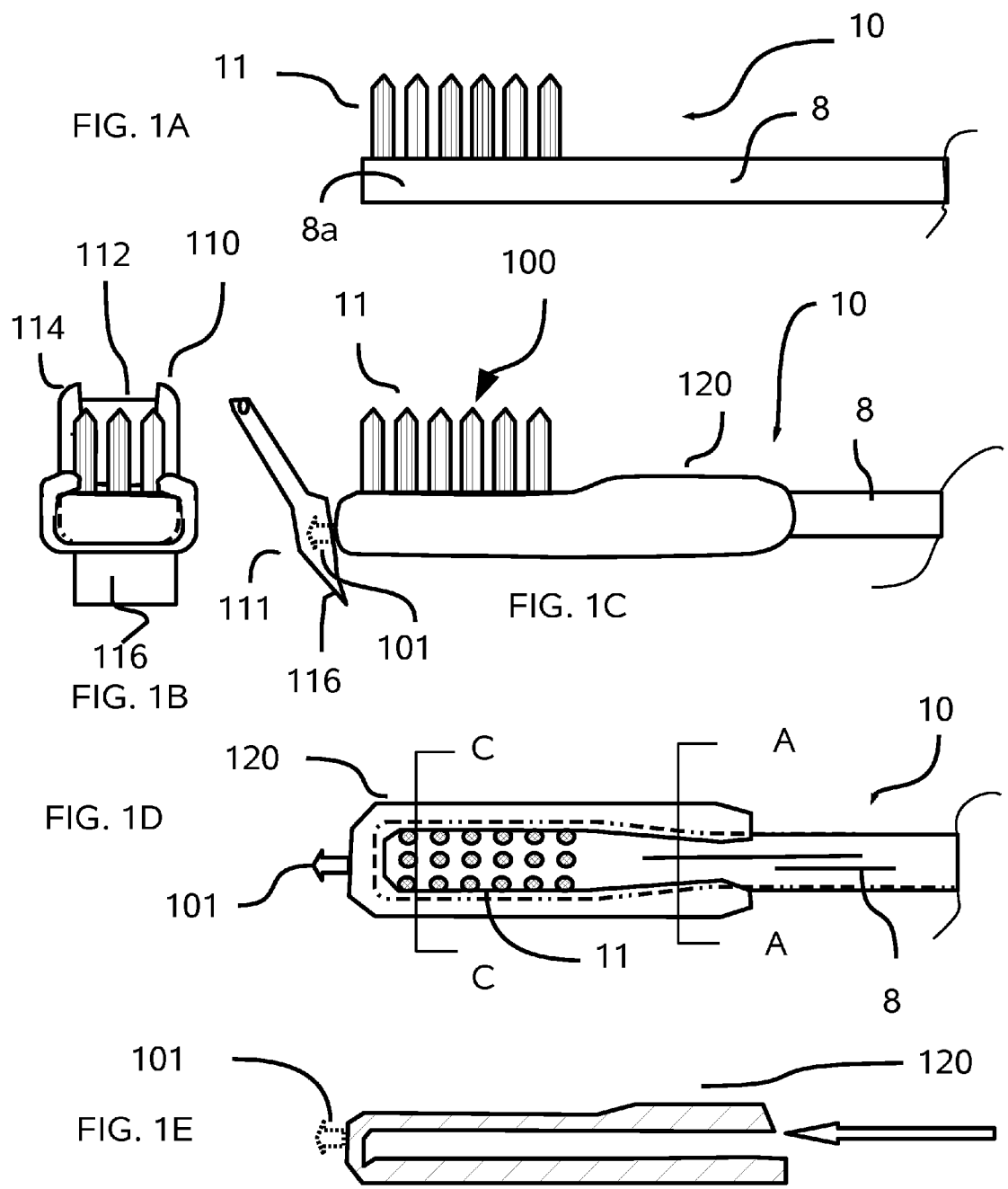

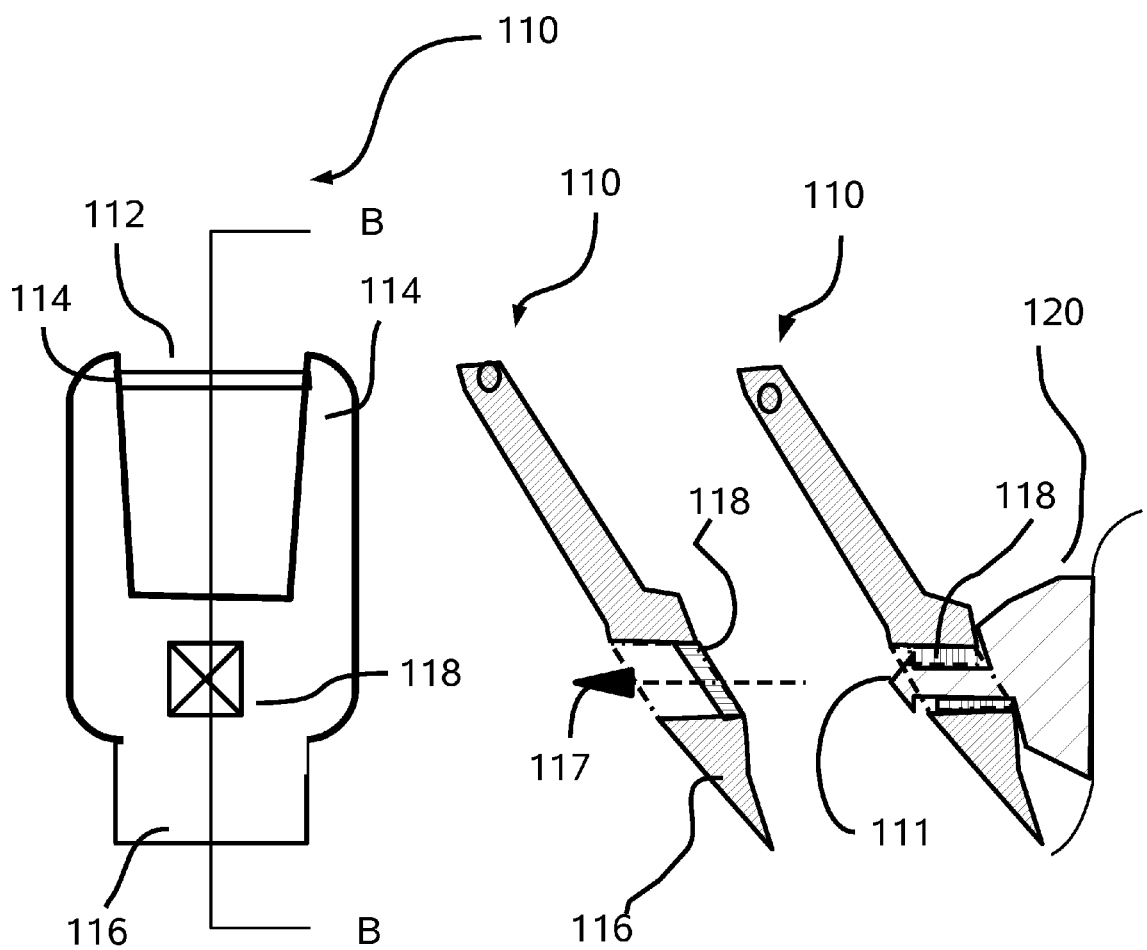

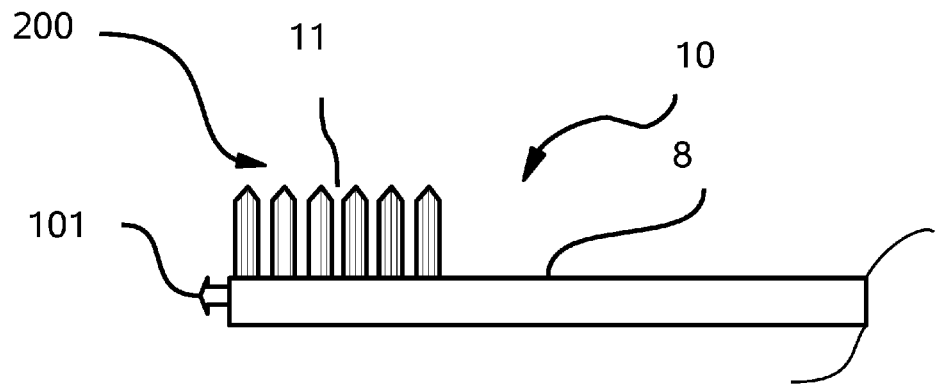
FIG. 4A
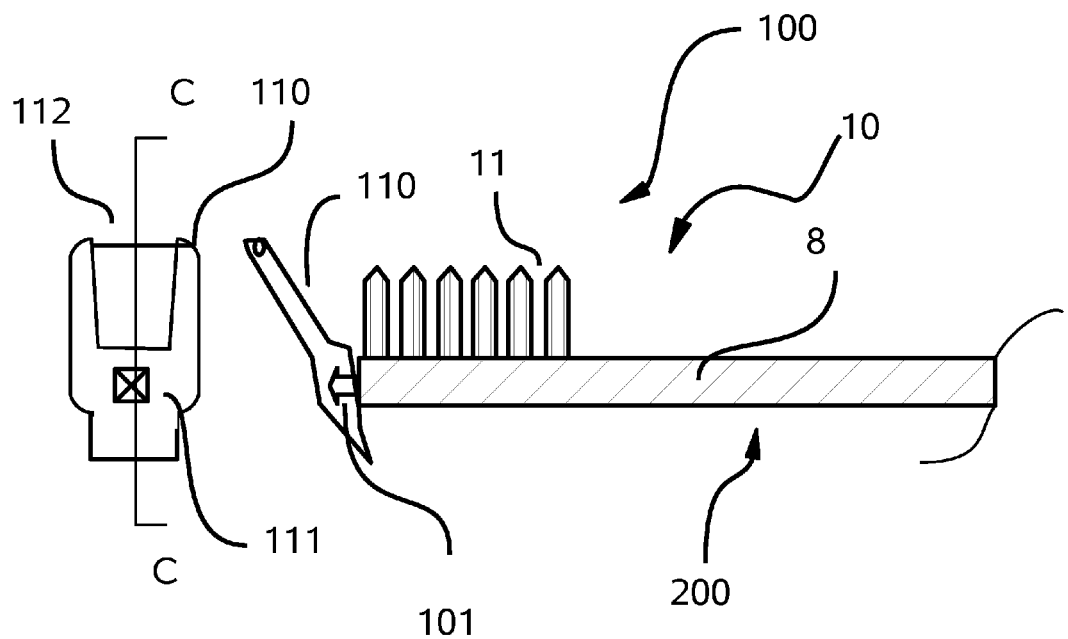
FIG. 4B
FIG. 4C

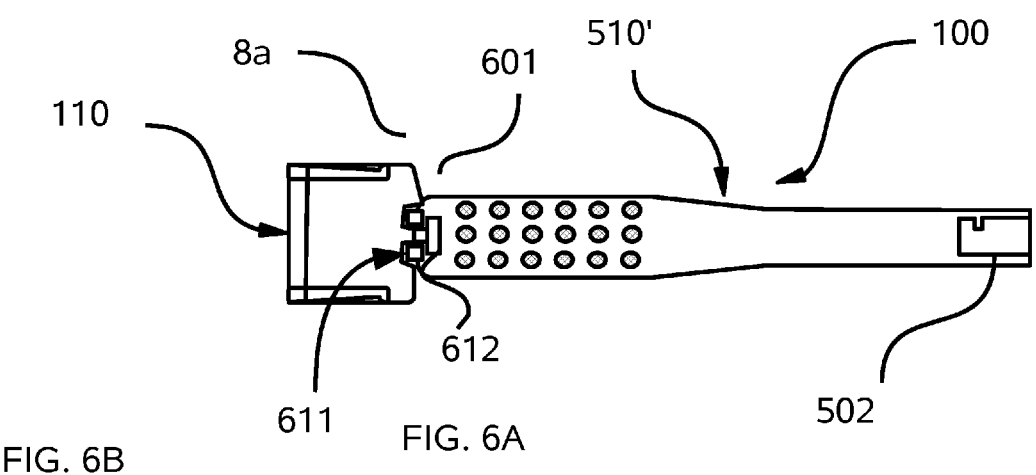
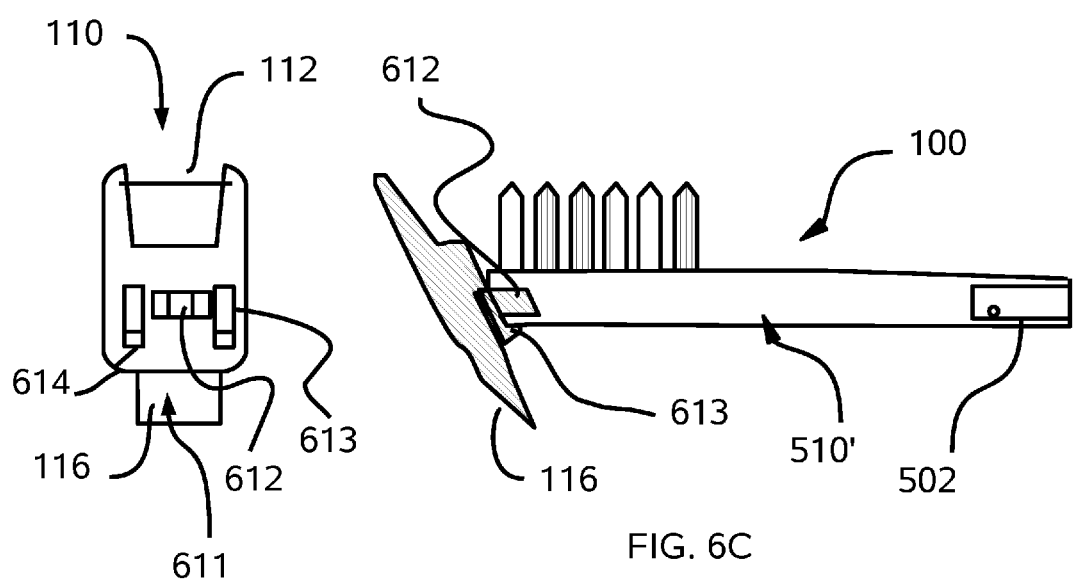

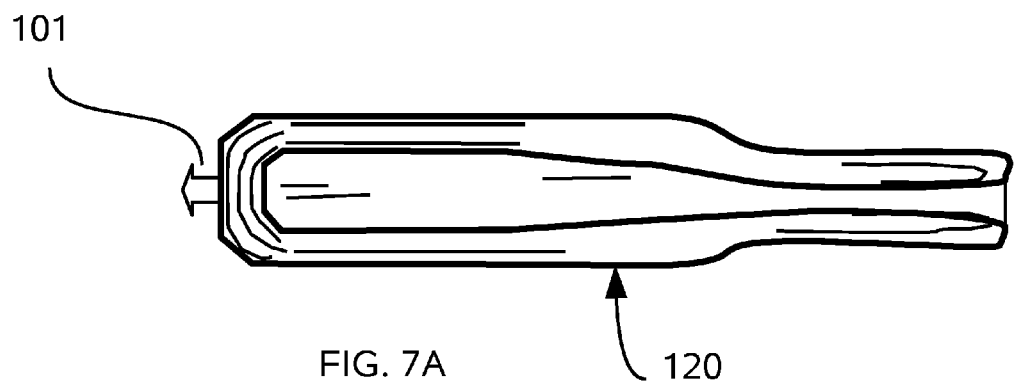
FIG. 7A
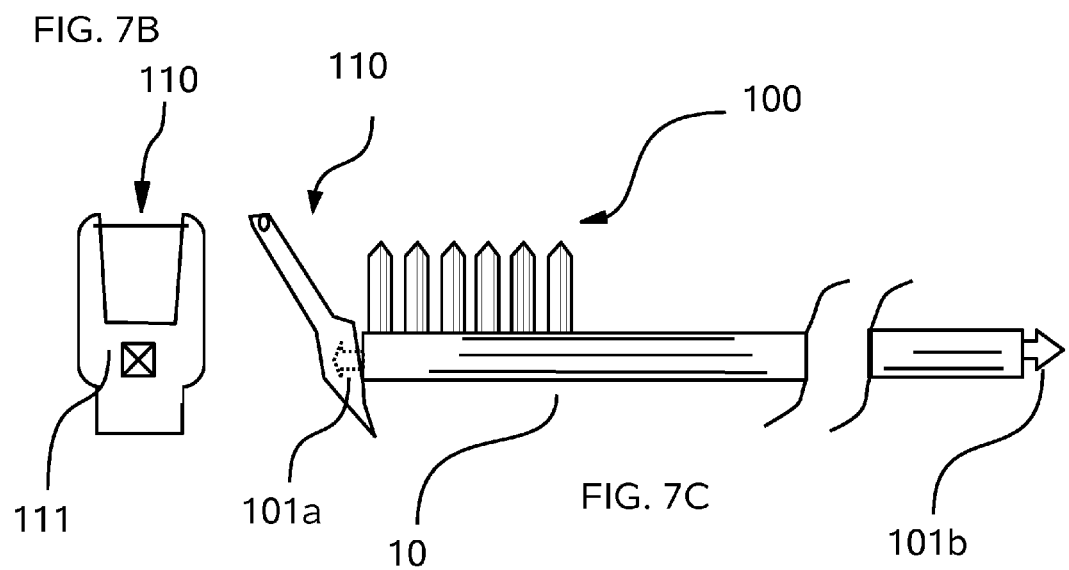
FIG. 7B
FIG. 7C

FLOSSING AND ORAL HYGIENE TOOL

CROSS REFERENCE TO RELATED APPLICATIONS

The present application claims priority to the US provisional application for a "Flossing and Oral Hygiene Tool" having application Ser. No. 60/978,036 and filed on Oct. 5, 2007, which is incorporated herein by reference.

BACKGROUND OF INVENTION

The present invention relates to oral hygiene tools and in particular device for flossing and relating oral hygiene attachments for a toothbrush.

It has been recognized in the art of oral hygiene devices that it would be convenient to provide multiple functionality in a single hand tool, that is a means to brush clean the exposed tooth surfaces as well as another tool, such as tensioned dental floss, to remove debris and/or plaque from below the portions of the gum line that are not reached by a brush.

Prior methods of providing dental floss and a tooth brush in a single device attempt to dispose the toothbrush and the dental floss at the opposite sides of a an elongated stick like handle than the brush. Exemplary design includes those disclosed in US Patent application Nos.'s: US2003188761; US2003005544; and US2006260635, as well as U.S. Pat. No. 5,924,429. A shortcoming of this design is that it is inconvenient to grip the tool on the brush side when flossing In an alternative approach, spooled dental floss is disposed on the same side of the handle as the brush, but on the back, opposite the brush. Such concepts are disclosed in U.S Pat. Nos. 6,772,770 and 6,095,157, as well as U.S Pat. Appl. No. US2002121283. The dental floss is generally tensioned on supports being threaded from a spool. However, in this design the spool and floss device can interfere with normal use of the tooth brush. Moreover, the bristles of the brush portion can interfere with the use of the dental floss. Such designs also present the problem that the spooled floss stored with or proximate the handle may be contaminated during use.

Another attempt to combine two oral hygiene devices is disclosed in U.S Pat. Appl. No. US20070100360 for a combination flossing device and tongue scraper. The device is essentially a pairs of tines that support tensioned dental floss. The tongue scraper is blade disposed opposite the tines and floss. In contrast, U.S Pat. Appl. NO. US200400237995 discloses a toothbrush having a hollow handle that conceals the refillable toothpaste, the dental floss and the tongue scraper. In contrast, the German with patent publication NO. DE19850325 discloses a dental care unit that comprises a sliding inter-dental brush, tooth pick and extensible dental floss set individually or all together in a head for fitting onto tooth brush. The inter-dental brush, tooth pick and floss can be turned to extend out and in by a rotary disc.

It should be noted that the aforementioned prior art does not provide a means for attaching a flossing device on a mechanical tooth brush head that the consumer chooses separately, such as an mechanical rotary tooth brush or ultrasonic tooth brush.

It should also be appreciated that the integrated designs of a flossing device in a tooth brush limits the consumers choice to a particular type of toothbrush, eliminating the options for a preference in a softness or the configuration of the bristles, as well as the option for use with an electric toothbrush of any type the consumer might already own.

It is therefore a first object of the present invention to provide a more flexible means for supplying a single device that allows floss and various oral hygiene aids to be attached or incorporated to a variety of toothbrushes, so as to encourage flossing as part of an oral hygiene regimen.

It is a further object of the invention to provide such a means wherein the brush and the floss holder/dispenser do not interfere with their respective operations.

It is a further object of the invention to provide such a device that is more hygienic in that the floss is not likely to be contaminated or used multiple times.

SUMMARY OF INVENTION

In the present invention, the first object of providing a means for providing a flossing attachment for use with different toothbrushes is achieved by providing a retrofitable flossing device, which comprises a floss head having a pair of tines extending upward from a base for supporting a string of dental floss in tension, the base including a first latchable fixture, and an at least partially flexible elongated adapter having a closed distal end and open proximal end with the intermediate portion between the distal and proximal ends having a generally U shaped cross-section to latchably receive the elongated distal portion of a tooth brush opposite the bristles wherein the closed distal end includes a second fixture for latchable engagement to the first latchable fixture of said floss head so as to dispose the dental floss outward from the tooth brush bristles.

It should be appreciated that the foregoing device provides a means for more efficient and effective sonic flossing, as the flexible adapter can be applied over a conventional toothbrush, or any sort of mechanical tooth brush head, including but not limited to a sonic toothbrush head.

A second aspect of the invention is characterized in a tooth brushing and flossing tool comprising an elongated brush handle having a proximal end for at least one of holding or attachment to a machine, and a distal end adapted for mated engagement of a floss head, an array of bristles extending substantially perpendicular from the side of the distal end of said elongated handle and rearward of the portion of the distal end adapted for mated engagement of a floss head, a floss head latchably engaged in the distal end of said elongated handle so as to dispose a length of tensioned dental floss forward of the array of bristles past the distal end of said elongated handle.

A third aspect of the invention is characterized by a disposable flossing head comprising a base member having a fixture for latchable engagement to an elongated handle, a pair of tines extending outward from the base member for tensioning a length of dental floss there between, wherein the fixture is oriented so as to dispose the tines at an oblique angle with respect to an elongated handle when so attached such that the dental floss is orientation transverse to the direction of the handle and extends outward and above the end of the handle attached to the flossing head.

Thus, it should be appreciated that in the various embodiments of the invention is provide alternative forms for a single device for flossing and cleaning tongue that promotes better hygiene. The disposable nature of the floss head in preferred embodiment prevents more than one use. Optionally, other embodiments may incorporates brush/floss/tongue cleaner/ inter dental cleaner into one device.

The above and other objects, effects, features, and advantages of the present invention will become more apparent from the following description of the embodiments thereof taken in conjunction with the accompanying drawings.

BRIEF DESCRIPTION OF THE DRAWINGS

FIG. 1A-E illustrates a first embodiment of the invention in which FIG. 1A is an elevation of a portion of the tooth brush prior to the fitting of an adapter and floss head.

FIG. 1B is an elevation of the floss head attached to the toothbrush of FIG. 1A via the adapter.

FIG. 1C is an elevation of the floss head attached to the adapter and toothbrush of FIG. 1A that is orthogonal to FIG. 1B.

FIG. 1D is a plan view of FIG. 1C prior showing the toothbrush and adapter prior to the attachment of the floss head.

FIG. 1E is a cross-sectional elevation of the adapter at reference line E-E in FIG. 2B.

FIG. 3A is an elevation of an embodiment of the floss head of FIG. 1B.

FIG. 3B is a cross-sectional elevation of the floss head orthogonal to the view in FIG. 3A prior to connection with an appropriate embodiment of the adaptor and is taken at reference line B-B in FIG. 3A.

FIG. 3C is the cross-sectional elevation of the floss head in FIG. 3B after the connection to an embodiment of the adaptor.

FIG. 4A is an elevation of a portion of a tooth brush modified for directly receiving the floss head.

FIG. 4B is an elevation of the floss head prior to attachment to the tooth brush of FIG. 4A.

FIG. 4C is a cross-sectional elevation of the floss head in FIG. 4B attached to the toothbrush in FIG. 4A taken at reference line C-C in FIG. 4B.

FIG. 6A is a plan view of another alternative embodiment of a tooth brush modified attached to an alternative embodiment of a floss head.

FIG. 6B is an elevation of alternative embodiment of a floss head in FIG. 6A.

FIG. 6C is a cross-section elevation of FIG. 6A that is orthogonal to the elevation of the floss head in FIG. 6B.

FIGS. 7A, B and C illustrate the components of a kit comprising the adapter (FIG. 7A; a plan view), floss head (FIG. 7B; an elevation) and the floss head engaged in an embodiment of a toothbrush adapted for receiving the same (FIG. 7C; an elevation orthogonal to FIG. 7B).

DETAILED DESCRIPTION

Figure 2A:
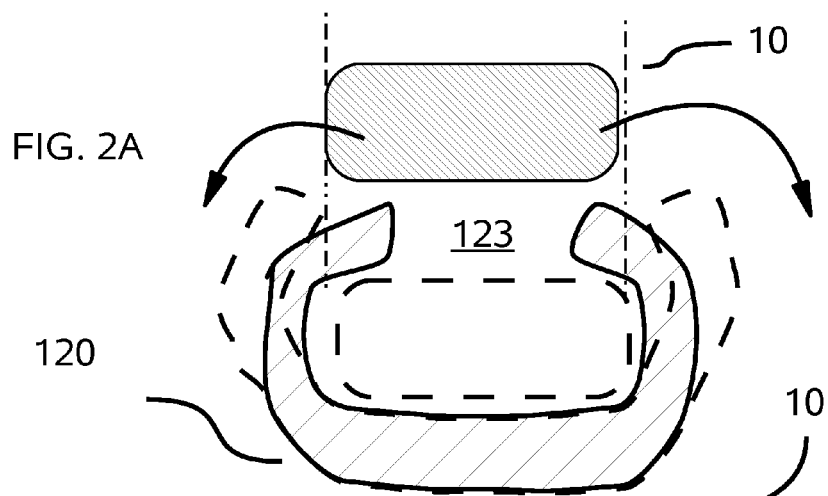
FIG. 2A is cross-sectional elevation through the adapter prior to insertion of the toothbrush corresponding to the position of the reference line A-A in FIG. 1D.

Referring to FIGS. 1 through 7, wherein like reference numerals refer to like components in the various views, there is illustrated therein a new and improved Flossing and Oral Hygiene Tool, generally denominated 100 herein.

FIG. 1A illustrates a tooth brush 10 having an elongated body 8 with bristles 11 extending outward from the distal end 8a, with the proximal end of the handle used for gripping not shown. FIG. 1C illustrates the Flossing and Oral Hygiene Tool or device 100 in which an adapter 120 attached to the bristle or distal end 8a of the toothbrush 10 to hold the floss head 110, shown in elevation in FIG. 1B. The floss head 110 comprises a pair of tines 114 that support a length of dental floss 112 in tension. Thus, using device 100, the floss 112 is disposed at the same end of the tooth brush as bristles 11, yet positioned sufficiently distal, that is outward from and generally above, so that distal end of the tooth brush 8a does not unduly interfere with flossing. More specifically, it has been discovered that although it is generally preferred that although the floss holder assembly disposes the floss sufficiently horizontally distal from the tooth brush head, about 5-10 mm, to avoid interference with flossing, it is actually desirable that the floss is positioned vertically close enough to the end of bristles so that the bristles will at least lightly touch the teeth during flossing. This is particularly useful to protect the gingival sulcus from damage when the floss snaps past a tight junction, which can occur as the user naturally applies greater force to overcome the resistance to the movement of the floss head. Thus, when the floss passes the tight junction, some bristles will ideally touch the upper tooth surface before the floss can recede far into the gum tissue, thus at least minimizing the potential for pain or damage to the gum tissue by de-accelerating the floss head as the bristles resist deformation.

Thus, it is generally preferred that the floss be placed between about 3-7 mm vertically above the top of the bristles.

Adapter 120 is generally tubular in shape but flattened and preferably closed at the end, having a wide slit 123 through which the bristles 11 extend when it engages the distal end 8a of the toothbrush 10. Adapter 120 wraps around the distal end of the tooth brush 10 on the side opposite bristles 11. It should be noted that the adapter 120 is intended to be made of a flexible material like a plastic or rubber so that it can be flexed opened before inserting distal end 8a of the toothbrush 10 as illustrated in FIG. 2.

Figure 2B:
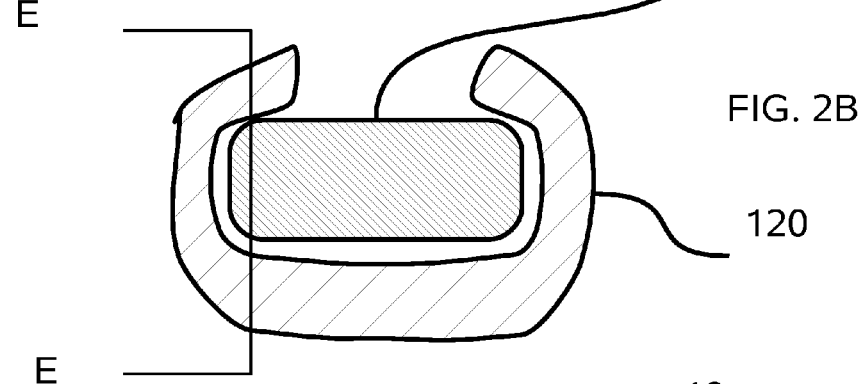
FIG. 2B is cross-sectional elevation through the adapter after insertion of the toothbrush taken at reference line A-A in FIG. 1D.
Figure 2C:
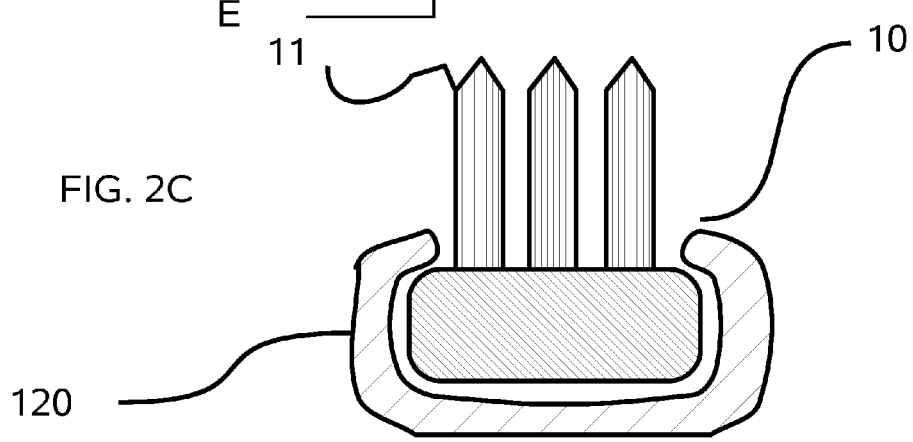
FIG. 2C is cross-sectional elevation of a different portion of the adapter (reference line C-C in FIG. 1D) after insertion of the toothbrush.

It can be seen in FIG. 2A then when the sides of the adapter flex open as indicated by the curved arrows, there is sufficient clearance to insert the wide distal end 8a of tooth brush 10. As the adapter is elastic, it ready snaps back in place surround the portion of tooth brush 10 near the bristles 11, as well as downward there from toward the proximal end, firmly engaging the tooth brush 10. It should be appreciated that the width and dimension of the slit and central bore of adapter 120 are preferable wide enough to accommodate a large range of commercial tooth brushes on the market, including without limitation various forms of electric and ultrasonic tooth brushes.

It will also be appreciated by one of ordinary skill in the art that the width and length of the adapter may be varied over a wide range and still fit a wide variety of commercial toothbrush sizes and shapes. However, to the extent that the adapter is target or intended for use with toothbrushes having a generally narrow handle it is more desirable that the adapter be sufficiently long and wide to effectively reinforce the toothbrush handle so that it does not unduly flex or possibly snap when the extra stress is placed on it for flossing. It should be noted that that the toothbrush or any other sort of extending floss holder handle will occasionally be subjected to high stress when the user is attempting to pass floss through a tight junction between teeth so that it can reach the margin of the teeth and gum tissue. It is also desirable that such an adapter accommodate smaller toothbrush sizes intended for children.

Further, it is preferable that edges of the slit in the adapter 120 that move apart are curved at the proximal end near the end grip portion of handle 8. This permits the insertion of the tooth brush by sliding it into the opening, distal end 8a first, in the direction of the arrow shown in FIG. 1E.

The adapter 120 has a locking member 101 for mating attachment to the floss head 110. Floss head 110 has a mating receiver 111 portion for coupling with locking member 101 on the adapter 120.

The floss head 110 is more fully illustrated in FIG. 3 and comprises a pair of tines 114 extending upward from a central or lower portion having the mating receiver 111 for the firm engagement with the locking member 101 extending from the closed end of adapter 120.

It should be appreciated that it is preferable that the mating receiver 111 and floss head 110 are configured to dispose the tines 114 upward and away from bristles 11 of toothbrush 10. More preferably, floss head 110 also comprise a tongue cleaning blade 116 opposite tines 114, extending in the opposite direction from mating receiver 111.

In this embodiment, the mating receiver 111 in floss head 110 has a square shaft or bore 117 that is covered on the side closest to adapter 120 with a scored series of four diagonal flaps 118. The corresponding locking member 101 of the adapter 120 in this embodiment is a barb. When the barb is inserted into floss head bore 117 in the direction of the arrow shown in FIG. 3B, the flaps 118 open and are deformed, bending laterally into bore 117. The flaps, being behind the barb 101, require a much larger force to remove the floss head 110 form the adapter 120. Thus, the floss head 110 is secured to the adapter 120 when the device 100 is used to floss the teeth. It should be noted that the position of the floss upward and away from bristles 11 facilitates access to all teeth, without interference and rubbing of the distal end 8a of tooth brush 10. It should be appreciated that it is also preferable that the barb 101 has a square or non-circular cross-section to prevent rotation of the floss head 110.

Further, it is also preferred that the floss head 110 must be replaced after it is removed from the adapter 120, so that it cannot be used multiple times to promote better hygiene. Thus, it is preferred that the flaps 118 readily tear away from bore 117 upon removing the floss head 110 by pulling in the opposite direction of the arrow shown in FIG. 3B, precluding an additional use. It should also be noted that the tongue cleaner blade 116 is disposed below tines 114 and thus has its principle axis disposed at an oblique angle with respect to a handle 8.

It should be appreciated that the device 100 of FIG. 1 allows a disposable tensioned dental floss to be attached to the toothbrush head, above and beyond the bristles of the toothbrush and avoiding having the bristles interfere with the flossing process. This can be accomplished either with the detachable adaptor 120 or by providing a barb or similar locking features 101 at the distal end 8a of the toothbrush 10, as is illustrated in FIG. 4. In FIG. 4A, an alternative embodiment of the device, now denominated 200, includes a toothbrush 10 with handle 8 and extending bristles 11. The barb that acts as locking device 101 extends from the edge of the handle 8 adjacent the bristles 11. The adapter 110 in FIG. 4B is then inserted via mating feature 11 onto the barb 101 to provide device 200 as shown in FIG. 4C. Thus, again flossing can occur using the bristle end of the tooth brush and avoid having the bristles interfere with the flossing process.

In more preferred embodiments the floss head 110 is mechanically coupled to (or incorporated into) a sonic toothbrush to transmit sonic energy to the floss 112 for improved cleaning. In other embodiments, the device 100 includes a tongue cleaning implement or blade 116, and in the alternative the ability to attach other inter dental cleaning devices, such as interproximal brushes, r-tips and the like.

Figure 5A:
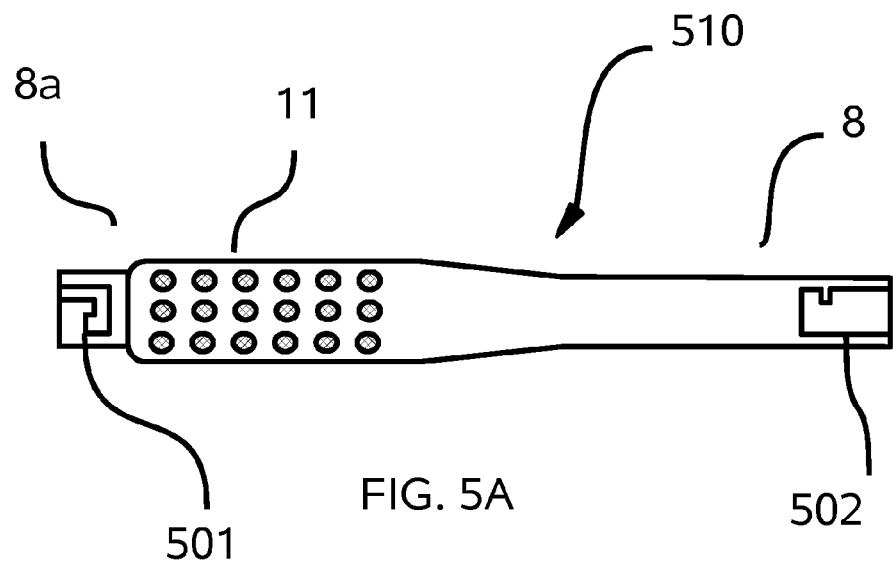
FIG. 5A is a plan view of an alternative embodiment of a tooth brush modified for directly receiving an alternative embodiment of a floss head.
Figure 5B:
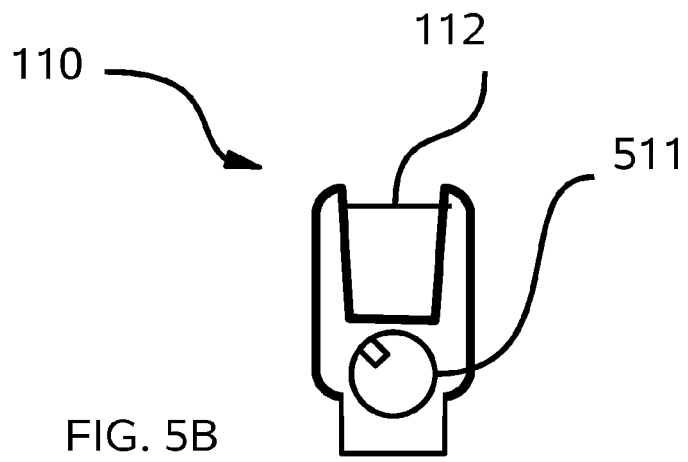
FIG. 5B is an elevation of alternative embodiment of a floss head for engaging the alternative embodiment of a tooth brush shown in FIG. 5A.

FIGS. 5 and 6 illustrate alternative embodiments of the invention for attaching the floss head to a brush apparatus. The toothbrush apparatus as shown in these figures also optionally includes means for attachment to an electronic toothbrush, such as an ultrasonic or rotating brush device, at the proximal end of handle 8 disposed opposite bristles 11. When the handle 8 is attached to an electric toothbrush sonic energy is transmitted to the dental floss 112 as well as the brush bristles 11.

In FIG. 5 the floss head 110 has a bayonet mount style mount 511. The distal end 8a of the toothbrush 510 also has a complimentary mating bayonet mount 501 wherein one of 510 and 501 is inserted onto the other and locks therewith in the conventional manner in which rotation is preferably followed by sliding apart in the opposite direction from the insertion. Optionally, the portion of the bayonet mount shown as 501, can alternatively be disposed on the floss head as 511, with portion 511 switched to handle 8. The means for mounting to an electric toothbrush 502 is also shown as a bayonet mount, but is intended to embrace alternative designs and configurations in current as well as future use by manufacturers of such products.

In FIG. 6 the floss head 110 the mating receiver 611 includes a T-shaped protrusion 612 while the toothbrush 10 has a corresponding locking mechanism 601 with a T-shaped slot in the end forward of or opposite the bristles 11.

The mating receiver 611 may also includes detents adjacent to the T-shaped protrusion 612 optionally in the form of one or more flexible arms 613 that terminated with short laterally extending barbs 614. When T-shaped protrusion 612 is slid into the corresponding slot in toothbrush 510' the arms 613 flex and then latch as the barbs 614 extend past the bottom surface of the toothbrush 510', opposite bristles 11.

It will be appreciated by one of ordinary skill in the art that suitable alternatives for the mating the T-shaped protrusion 612 and slot include any alternative shapes for sliding engagement, such as one or more matching teeth, a serpentine type path and the like. Further it should be appreciated that it may be preferable in some instances for the toothbrush to have a recess and not a protrusion, deposing on the exact configuration of these complimentary mating features the position may be reversed.

In another embodiment shown in FIG. 7, there is a kit that comprises the adapter 120 suitable for use with any toothbrush, including mechanical electric or ultrasonic toothbrush, one or more floss heads 110, as well as a toothbrush 10 having at least one mating or locking feature 101a (in this case illustrated for exemplary purposes by a barb) at the distal end to receive the floss heads 110 at its complimentary receiver 111. Further, In FIG. 7C the proximal end of tooth brush optionally has a rear mating or locking feature 101b (such as a barb and the like) so that the floss head 110 can be attached to either end of the toothbrush 10.

While the invention has been described in connection with a preferred embodiment, it is not intended to limit the scope of the invention to the particular form set forth, but on the contrary, it is intended to cover such alternatives, modifications, and equivalents as may be within the spirit and scope of the invention as defined by the appended claims. Thus, for example in addition to the alternative embodiments already described the tooth brush may have any style or array of bristles, such as rotary bristles as well as static bristles. Further, it should be understood that while it is preferable that floss 112 is pre-molded into the tines 114, it is alternatively continuously thread able between the tine ends.

The invention claimed is:

1. A retrofitable flossing device, which comprises:
   a) a floss head having a pair of tines extending upward from a base for supporting a string of dental floss in tension, the base including a first latchable fixture,
   b) an at least partially flexible elongated adapter having a closed distal end and an open proximal end with the intermediate portion between the distal and proximal ends having a generally U shaped cross-section to provide an open upper portion to latchably receive the elongated distal portion of a tooth brush opposite the bristles such that all of the bristles can extend through the open upper portion wherein the closed distal end includes a second fixture for latchable engagement to the first latchable fixture of said floss head so as to dispose the dental floss outward from the tooth brush bristles.

2. A retrofitable flossing device according to claim 1 wherein said floss head is precluded from rotating about the elongated adapter after attachment thereto.

3. A retrofitable flossing device according to claim 1 wherein the first latchable fixture of said floss head is distorted after removal from said elongated adapter to preclude multiple uses thereof.

4. A retrofitable flossing device according to claim 1 wherein said floss head further comprises disposed opposite the pair of tines at least one implement selected from the group consisting of a tongue cleaning implement or blade, an interproximal brush and r-tip.

5. A retrofitable flossing device according to claim 2 wherein the first latchable fixture of said floss head is distorted after removal from said elongated adapter to preclude multiple uses thereof.

6. A retrofitable flossing device according to claim 2 wherein said floss head further comprises a tongue scraping blade opposite the pair of tines.

7. A retrofitable flossing device according to claim 3 wherein said floss head further comprises a tongue scraping blade opposite the pair of tines.

8. A retrofitable flossing device according to claim 1 wherein said tooth brush bristles terminate in bristle tips and the vertical distance between the floss and the bristle tips is not more than about 5 mm.

9. A tooth brushing and flossing tool comprising
   a) an elongated brush handle having a proximal end for at least one of holding or attachment to a machine, and a distal end adapted for mated engagement of a floss head, wherein the distal end has a first side and a second side opposite the first side,
   b) an array of bristles extending substantially perpendicular from first side of the distal end of said elongated handle terminating at tips, the array being disposed rearward of the portion of the distal end adapted for mated engagement of the floss head,
   c) a floss head having a latchable fixture means so as to be latchably engaged in the distal end of said elongated handle so as to dispose on the first side of the elongated brush handle a length of tensioned dental floss forward of the array of bristles and past the distal end of said elongated brush handle.

10. A tooth brushing and flossing tool according to claim 9 wherein said floss head is precluded from rotating about the distal end of said elongated handle after attachment thereto.

11. A tooth brushing and flossing tool according to claim 9 wherein the latchable fixture of said floss head is distorted after removal from said brush handle to preclude multiple uses thereof.

12. A tooth brushing and flossing tool according to claim 10 wherein said floss head further comprises a tongue scraping blade disposed on the second side of the elongated brush handle.

13. A tooth brushing and flossing according to claim 10 wherein the vertical distance between the tensioned dental floss and the bristle tips is not more than about 5 mm.

14. A tooth brushing and flossing according to claim 11 comprises a tongue scraping blade disposed on the second side of the elongated brush handle.

15. A disposable flossing head comprising:
   a) a base member having a fixture for latchable engagement to an elongated handle having a primary axis,
   b) a pair of tines extending outward from the base member for tensioning a length of dental floss there between, wherein each tine extends along a first axis and dental floss is oriented in a second axis, the second axis being orthogonal to the first axis,
   c) wherein the fixture when attached to the elongated handle is oriented to dispose the first axis of each tine at an oblique angle with respect to the primary axis of the elongated handle such that the second axis of the dental floss is oriented transverse to the primary axis of the elongated handle with the end of both tines that define the secondary axis extending and above the end of the elongated handle attached to the flossing head,
   wherein the fixture for latchable engagement of said base member is distorted after removal from said elongated handle to preclude multiple uses thereof.

16. A disposable flossing head according to claim 15 wherein said floss head further comprises a tongue scraping blade disposed on the side thereof opposite said pair of tines.

17. A kit for dental hygiene comprising:
   a) a toothbrush having a forward end with bristles extending outward from a portion thereof that defines a tooth brush head and a distal end opposite the forward end which provides a grippable portion, wherein the forward end or the distal end has a first latch to receive a mating disposable floss head,
   b) an adapter means for fitting around a tooth brush head, having a forward latch to receive a mating disposable floss head,
   c) one or more disposable floss heads having a fitting to couple with both the first latch and the forward latch.

18. A kit for dental hygiene according to claim 17 wherein the fitting of the disposable floss head is distorted after removal from the first latch to preclude reattachment to the first latch after removal therefrom.

19. A disposable flossing head according to claim 15 wherein said floss head is precluded from rotating about the elongated handle after attachment thereto.

20. A kit for dental hygiene according to claim 17 wherein said floss head is precluded from rotating about the toothbrush or adapter means after attachment thereto.

* * * * *